US007860897B2

(12) United States Patent
Dettinger et al.

(10) Patent No.: US 7,860,897 B2
(45) Date of Patent: Dec. 28, 2010

(54) OPTIMIZED METHOD OF LOCATING COMPLETE AGGREGATION OF PATIENT HEALTH RECORDS IN A GLOBAL DOMAIN

(75) Inventors: Richard D. Dettinger, Rochester, MN (US); Daniel P. Kolz, Rochester, MN (US); Richard J. Stevens, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 954 days.

(21) Appl. No.: 11/241,697

(22) Filed: Sep. 30, 2005

(65) Prior Publication Data

US 2007/0078856 A1 Apr. 5, 2007

(51) Int. Cl.
*G06F 17/30* (2006.01)
*G06F 15/16* (2006.01)

(52) U.S. Cl. ........................ 707/803; 709/203; 709/219

(58) Field of Classification Search ..................... 707/1, 707/10, 803, 999.102; 705/2, 3; 709/203, 709/219
See application file for complete search history.

(56) References Cited

U.S. PATENT DOCUMENTS

| | | | | |
|---|---|---|---|---|
| 5,327,508 | A * | 7/1994 | Deaton et al. | 382/100 |
| 5,452,445 | A * | 9/1995 | Hallmark et al. | 707/2 |
| 5,457,689 | A * | 10/1995 | Marvit et al. | 370/449 |
| 5,805,798 | A * | 9/1998 | Kearns et al. | 714/48 |
| 5,813,009 | A * | 9/1998 | Johnson et al. | 707/100 |
| 5,995,965 | A * | 11/1999 | Experton | 707/10 |
| 6,049,861 | A * | 4/2000 | Bird et al. | 712/28 |
| 6,072,942 | A * | 6/2000 | Stockwell et al. | 709/206 |
| 6,101,541 | A * | 8/2000 | Ellesson et al. | 709/225 |
| 6,263,330 | B1 * | 7/2001 | Bessette | 707/4 |
| 6,335,937 | B1 * | 1/2002 | Chao et al. | 370/426 |
| 6,556,999 | B1 * | 4/2003 | Kloos et al. | 707/10 |
| 6,775,670 | B2 * | 8/2004 | Bessette | 707/10 |
| 7,076,521 | B2 * | 7/2006 | Davison | 709/203 |

(Continued)

FOREIGN PATENT DOCUMENTS

EP 1-077-415 A1 * 2/2001

(Continued)

OTHER PUBLICATIONS

Brelstaff, Gavin, et al., "Internet Patient Records: New Techniques", Journal of Medical Internet Research, vol. 3, No. 1, Jan.-Mar. 2001, pp. 1-18.*

(Continued)

*Primary Examiner*—Robert Stevens
(74) *Attorney, Agent, or Firm*—Patterson & Sheridan, LLP

(57) ABSTRACT

A method, apparatus, and article of manufacture are provided to optimize the time and effort required to locate all data on a given entity that may span multiple data nodes in a distributed environment. For example, embodiments of the invention may be used to locate nodes within the distributed environment that store electronic healthcare records. A poll request from a first node to a second node may include electronic records existence data indicating data nodes known to have, or not have, records related to a given individual. This information is used to minimize the number of nodes that need to be polled to arrive at the complete aggregation of patient records that exist within a given set of nodes.

11 Claims, 6 Drawing Sheets

U.S. PATENT DOCUMENTS

| | | | | |
|---|---|---|---|---|
| 7,720,691 | B2 * | 5/2010 | Hasan et al. | 705/2 |
| 2001/0016822 | A1 * | 8/2001 | Bessette | 705/3 |
| 2002/0019751 | A1 * | 2/2002 | Rothschild et al. | 705/3 |
| 2002/0032720 | A1 * | 3/2002 | Nelson et al. | 709/201 |
| 2002/0066026 | A1 * | 5/2002 | Yau et al. | 713/201 |
| 2002/0103811 | A1 * | 8/2002 | Fankhauser et al. | 707/104.1 |
| 2003/0088438 | A1 * | 5/2003 | Maughan et al. | 705/2 |
| 2003/0101238 | A1 * | 5/2003 | Davison | 709/219 |
| 2003/0182421 | A1 * | 9/2003 | Faybishenko et al. | 709/224 |
| 2004/0083129 | A1 * | 4/2004 | Herz | 705/10 |
| 2004/0098390 | A1 * | 5/2004 | Bayliss et al. | 707/7 |
| 2004/0153440 | A1 * | 8/2004 | Halevy et al. | 707/3 |
| 2004/0267927 | A1 * | 12/2004 | Davis et al. | 709/224 |
| 2005/0060195 | A1 * | 3/2005 | Bessette et al. | 705/2 |
| 2005/0216313 | A1 * | 9/2005 | Claud et al. | 705/3 |
| 2006/0089539 | A1 * | 4/2006 | Miodownik et al. | 600/300 |
| 2006/0168002 | A1 * | 7/2006 | Chesley | 709/205 |
| 2006/0168338 | A1 * | 7/2006 | Bruegl et al. | 709/240 |
| 2006/0229911 | A1 * | 10/2006 | Gropper et al. | 705/2 |
| 2006/0259468 | A1 * | 11/2006 | Brooks et al. | 707/3 |
| 2007/0027715 | A1 * | 2/2007 | Gropper et al. | 705/2 |
| 2007/0055552 | A1 * | 3/2007 | St. Clair et al. | 705/3 |
| 2007/0192140 | A1 * | 8/2007 | Gropper | 705/3 |
| 2007/0214018 | A1 * | 9/2007 | Claud | 705/3 |

FOREIGN PATENT DOCUMENTS

WO 03/038731 A2 5/2003

OTHER PUBLICATIONS

Witting, Karen, et al., "HCLS IHII Phase 1 Architecture Document, Rev. 5", IBM Health care and Life Sciences, Aug. 23, 2005, pp. 1-22.*

Forslund, David, et al., "The Virtual Patient Record: A Key to Distributed Healthcare and Telemedicine", Los Alamos National Laboratory, Feb. 29, 1996, pp. 1-5.*

Sittig, Dean F., et al., "A Draft Framework for Measuring Progress Towards the Development of a National Health Information Infrastructure", BMC Medical Informatics and Decision Making, vol. 5, No. 14, Jun. 13, 2005, pp. 1-8.*

Kilman, David G., et al., "An International Collaboratory Based on Virtual Patient Records", RIDE-VE '99, Sydney, Australia, Mar. 23-24, 1999, pp. 148-155.*

"ACC, HIMSS and RSNA: Integrating the Healthcare Enterprise (IHE) IT Infrastructure Technical Framework, vol. 1 Integration Profiles, Rev. 2", Aug. 15, 2005, pp. cover and 1-134.*

"ACC, HIMSS and RSNA: Integrating the Healthcare Enterprise (IHE) IT Infrastructure Technical Framework, vol. 2 Transactions, Rev. 2", Aug. 15, 2005, pp. cover and 1-282.*

Fontijn, Willem, et al., "AmbientDB: P2P Data Management Middleware for Ambient Intelligence", PERCOMW '04, Mar. 14-17, 2004, pp. 1-6.*

Massie, Matthew L., et al., "The Ganglia Distributed Monitoring System: Design, implementation and Experience", Parallel Computing, vol. 30, Issue 7, Jul. 2004, pp. 817-840.*

Tolchin, S. G., et al., "The Distributed Processing Approach to Hospital Information Processing", Journal of Medical Systems, vol. 5, No. 4, Dec. 1981, pp. 345-360.*

Hertzberg, Richard Y., et al., "Abstract: The PROMIS Network", Computer Networks, vol. 4, Issue 5, Oct. / Nov. 1980, 3 pages.*

McDaniel, James G., "Discrete-event Simulation of a Wide-area Health Care Network", Journal of the American Medical Informatics Association, vol. 2, No. 4, Jul. / Aug. 1995, pp. 220-237.*

Working Group on Accurately Linking Information for Health Care Quality and Safety, "Linking Health Care Information: Proposed Methods for Improving Care and Protecting Privacy", Feb. 2005, XP002412449, Retrieved from the Internet, http://www.connectingforhealth.org/assets/reports/linking_report_2_2005.pdf.

Alschuler, L, et al., "HL7 NLM Interoperability Survey", Jul. 18, 2005, XP002412450, retrieved from the Internet, http://www.alschulerassociates.com/library/documents/HL7NLMSurvey_FINAL.pdf.

Farrukh Najmi: "Web Content Management Using the OASIS ebXML Registry Standard", Feb. 2, 2004, XP002412451, retrieved from http://ebxmlrr.sourceforge.net/presentations.xmlEurope2004/04-02-02.pdf.

Garbacki P et al, "A Two-Level Semantic Caching Scheme for Super-Peer Networks", Web Content Caching and Distribution, 2005, ISBN: 0-7695-2455-9.

Botros S et al, "Search in JXTA and Other Distributed Networks", Peer-To-Peer Computing 2001, ISBN: 0-7695-1503-7, (c) 2002.

Androutselli-Theotokis S, et al, "A Survey of Peer-to-Peer Content Distribution Technologies" ACM Computing Surveys ACM USA, vol. 36, No. 4, Dec. 2004, pp. 335-371, XP002412530, ISSN: 0360-0300X.

Eltrun Athens University of Economic and Business: "Eltrun White Paper: A Survey of Peer-to-Peer File Sharing Technologies", XP007901251, retrieved from the Internet, http://www.cs.ucr.edu/{michalis/COURSES/179-03/p2psurvey.pdf>, (c) 2002.

Crespo A, et al, "Routing Indices for Peer-to-Peer Systems" Proceedings of the 22nd International Conference on Distributed Computing Systems, ISBN 0-7695-1585-1, Feb. 7, 2002.

Nejdl, W, et al, Super-Peer-Based Routing and Clustering Strategies for RDF-Based Peer-to-Peer Networks, The Twelfth International World Wide Web Conference (WWW2003), XP002412560, May 2003.

* cited by examiner

OPTIMIZED METHOD OF LOCATING COMPLETE AGGREGATION OF PATIENT HEALTH RECORDS IN A GLOBAL DOMAIN

BACKGROUND OF THE INVENTION

1. Field of the Invention

The present invention generally relates to data storage and retrieval. More specifically, the present invention relates to retrieving electronic data records related to a given subject, when such records may be distributed among many locations.

2. Description of the Related Art

Electronic data is pervasive; electronic data records have been created to capture details about almost every transaction or event that occurs. Often however, electronic data is highly dispersed. For example, electronic medical records regarding a specific individual may exist in many locations. For example, an outpatient clinic may maintain a set of electronic records for individual patients treated by the clinic; a hospital emergency room may have data related to the same patient; while at the same time, a pharmacy may maintain records for prescriptions issued by both the clinic and the emergency room. In most cases, these providers will not have access to the electronic records of one another. As even this simple example illustrates, electronic medical records related to a patient may be widely distributed across many entities.

In many cases, it would be useful to provide access to a comprehensive set of electronic medical records related to a given individual, including records that may be widely distributed across multiple entities. Doing so, however, has proven to be a difficult endeavor. One proposed method includes creating a national health information infrastructure from many regional networks, wherein each regional network shares access to (or stores) electronic health records among a number of participants. Once established, these regional networks (referred to herein as RHIOs, for Regional Health Information Organization) may be connected to form a nation-wide infrastructure. Thus, a national health information network may emerge from a specialized "network of networks," making electronic medical records available to health care providers when and where they are needed.

One significant problem faced in creating such a national (or larger) infrastructure, however, is locating a comprehensive collection of electronic healthcare records for an individual patient that has records spanning multiple data nodes. For example, consider a common scenario of treating an unconscious patient at a hospital emergency room. In such a case, a treating physician may desire access to a complete set of medical records regarding the patient to determine a course of treatment, regardless of where the records are located. The physician may, or may not, know which RHIO is associated with the patient's primary care physician, but is unlikely to know a complete set of data nodes that have medical records related to the patient.

One approach to sharing electronic medical records among multiple RHIOs involves connecting the individual RHIOs using a nationwide master patient index and registry that identifies which RHIOs contain electronic records for an individual. In this case, the physician seeking records for the unconscious patient would access the master patient index to identify the various RHIOs that have electronic records regarding the patient. However, both technical and social barriers may make this an inadequate (or impossible) solution. First, the cost of the infrastructure required to implement such a solution may be prohibitive. Second, political and social concerns regarding patient privacy and the security of electronic medical records may prevent this approach from ever being practical, regardless of the technical obstacles and cost of implementing it. Moreover, the master patient index may create a single point of failure for the entire system; should the master patient index and registry become unavailable (e.g., for technical reasons), participants within an individual RHIO would be unable to locate electronic records using the master patient index.

Another approach to locating a comprehensive collection of medical records for an individual patient is to perform a brute force search of hundreds, or even thousands, of RHIOs in an attempt to locate records related to a given individual. However, this approach will often become very time consuming and inefficient, especially in situations where life-or-death decisions must be made quickly, or when used repeatedly for multiple searches related to the same individual.

Accordingly, the approach of creating a national health care records infrastructure from a "network of networks" presents the challenge of how to locate records related to a given individual when the records may be dispersed across many of the different networks. Using the RHIO as an example, in connecting hundreds, or thousands, of RHIOs, a requesting party must be able to efficiently determine which RHIOs contain electronic records for a given individual.

SUMMARY OF THE INVENTION

Embodiments of the invention provide techniques to optimize the time and effort required to locate electronic records related to a given entity when the records may span multiple data nodes in a distributed environment. For example, embodiments of the invention may be used to perform searches that span multiple RHIOs for electronic medical records related to a given patient.

One embodiment of the invention provides a computer-implemented method of accessing a plurality of electronic records associated with an identified subject, wherein the electronic records may exist in a plurality of independent data nodes. The method generally includes, receiving, from a first data node, a response to a poll request, wherein the response includes an indication of whether records regarding the identified subject are available in the first data node, and polling at least a second data node to determine an availability of electronic records regarding the identified subject at the second data node, wherein the poll transmitted to the second data node includes the indication received from the first node. The plurality of independent data nodes may include electronic healthcare records available from geographically distributed nodes.

The indication received from the first node may also indicate additional nodes, from the plurality of independent data nodes, known to have, or to not have, electronic records regarding the identified subject. Further, the poll request may transmit an indication of additional nodes, from the plurality of independent data nodes, known to have, or to not have, electronic records regarding the identified subject.

Another embodiment of the invention provides a computer-readable medium containing a program, which when executed on a computer system performs operations for accessing a plurality of electronic records associated with an identified subject, wherein the electronic records may exist in a plurality of independent data nodes. The operations generally include receiving, from a first data node, a response to a poll request, wherein the response includes an indication of whether records regarding the identified subject are available in the first data node, and polling at least a second data node to determine an availability of electronic records regarding the identified subject at the second data node, wherein the poll transmitted to the second data node includes the indication received from the first node. The plurality of independent data nodes may include electronic healthcare records available from geographically distributed nodes.

Still another embodiment includes a system for accessing a plurality of electronic records associated with an identified subject. The system generally includes a plurality of computer-accessible independent data nodes, wherein each node includes a data locator configured to perform operations for accessing a plurality of electronic records associated with an identified subject, wherein the electronic records may exist in the plurality of independent data nodes. The operations generally include receiving, from a first data node, a response to a poll request, wherein the response includes an indication of whether records regarding the identified subject are available in the first data node, and polling at least a second data node to determine an availability of electronic records regarding the identified subject at the second data node, wherein the poll transmitted to the second data node includes the indication received from the first node. The plurality of independent data nodes may include electronic healthcare records available from geographically distributed nodes.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments illustrated by the appended drawings. These drawings, however, illustrate only typical embodiments of the invention and are not limiting of its scope, for the invention may admit to other equally effective embodiments.

DETAILED DESCRIPTION OF THE PREFERRED EMBODIMENTS

Figure 1:
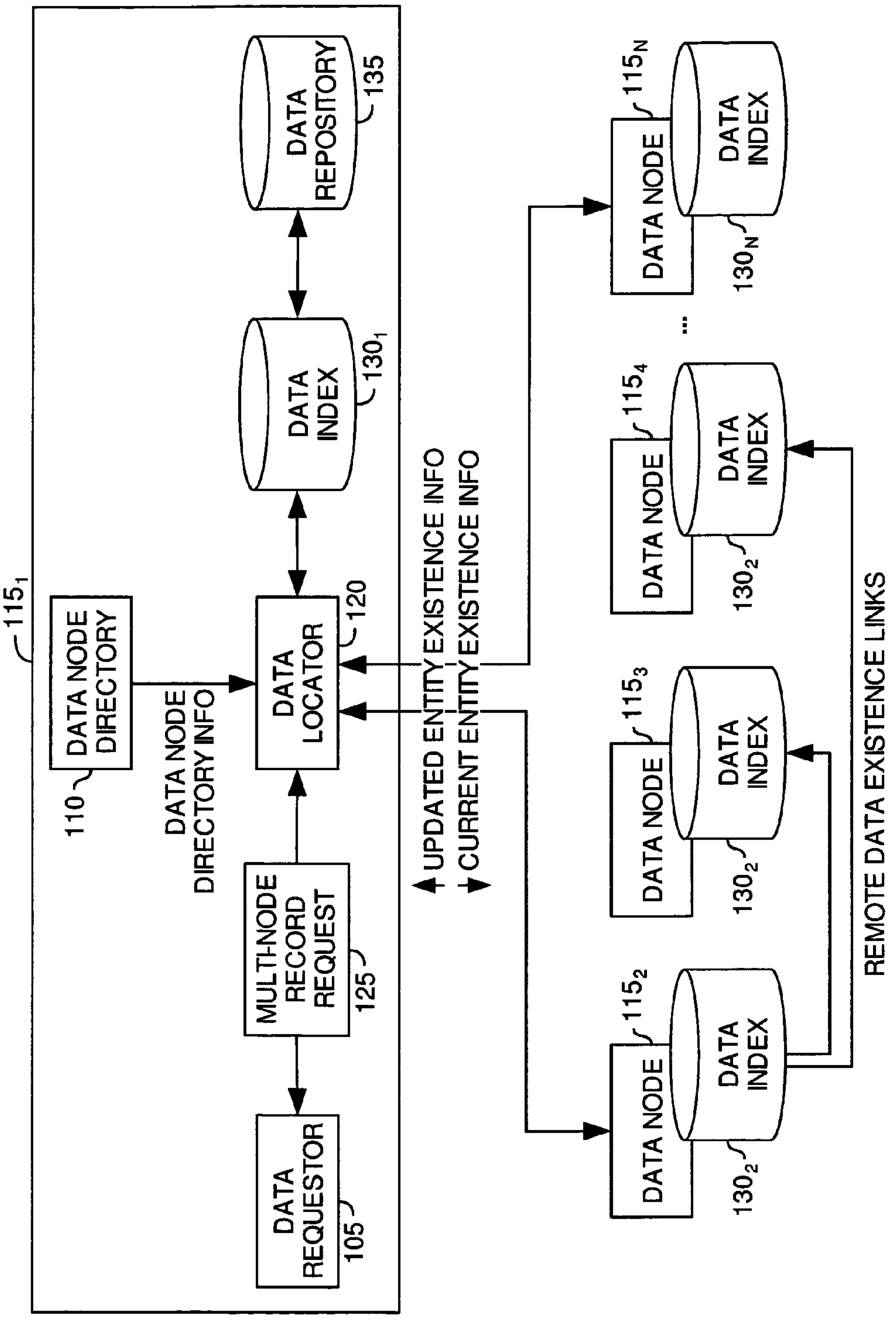
FIG. 1 illustrates data communications occurring in a distributed environment, according to one embodiment of the invention.

The present invention provides methods, systems, and articles of manufacture to optimize the time and effort required to locate a comprehensive collection of electronic records related to a given entity in situations where the electronic records may be stored in multiple data nodes across a distributed environment.

For example, embodiments of the invention may be used to perform searches for electronic medical records that span multiple regional health Information organizations (RHIOs). In such a scenario, embodiments of the invention optimize the task of locating a comprehensive collection of electronic health records that exist across one or more RHIOs. In one embodiment, the query grammar used to compose a query may include conditions used to select a set of RHIOs to poll for the existence of electronic records related to a given individual.

Additionally, a RHIO may be configured to maintain a master index specifying the individuals that have electronic records stored within the RHIO. At the same time, the RHIO may also maintain information regarding other RHIOs known to have (or to not have) records regarding a given individual. This additional information may be used to minimize the number of RHIOs that are polled to identify where the electronic records related to an individual are stored. If a given RHIO is known to have, or to not have electronic records related to an individual, then the given RHIO need not be polled in order to determine its status. Additionally, a polling RHIO may include information regarding RHIOs known to have, or to not have, with a poll request. Examples of these scenarios are described more fully below.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Embodiments of the invention may be implemented, in part, using computer software applications executing on existing computer systems, e.g., desktop computers, server computers, laptop computers, tablet computers, and the like. The data communications techniques and distributed data nodes described herein, however, are not limited to any currently existing computing or data communications environment, and may be adapted to take advantage of new computing systems as they become available.

Further, embodiments of the invention (including the methods described herein) may be implemented as computer software applications and can be contained on a variety of computer-readable media. Illustrative computer-readable media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks wi a diskette drive or hard-disk drive); or (iii) information conveyed to a computer by a communications medium, such as through a computer or telephone network, including wireless communications. The latter embodiment specifically includes information across the Internet and other data communications networks. Such computer-readable media, when carrying computer-readable instructions that direct the functions of the present invention, represent embodiments of the present invention.

In general, program routines created to implement an embodiment of the invention may be part of an operating system or a specific application, component, program, module, object, or sequence of executable instructions performed by a particular computing system. In addition, various computer software applications described hereinafter may be identified based upon the application for which they are implemented in a specific embodiment of the invention. However, it should be appreciated that any particular program nomenclature that follows is used merely for convenience, and thus the invention is not limited to use solely in any specific application identified and/or implied by such nomenclature.

FIG. 1 illustrates a data communications environment 100 configured to locate data records related to a given entity spread across multiple data nodes $\mathbf{115}_{1-n}$, according to one embodiment of the invention. Illustratively, the environment 100 includes five data nodes 115, each having access to a collection of electronic records.

In one embodiment, each data node 115 may store records regarding a plurality of entities. Further, embodiments of the invention may allow a data requestor 105 to locate all of the records related to a given entity, which may exist in multiple data nodes 115. For simplicity, the discussion herein assumes that the entity is an individual, and the data stored by data nodes 115 may include electronic records related to many individuals. However, embodiments of the invention that store data related to other entities are contemplated. Additionally, for purposes of illustration, node 1151 may be referred to as a "local data node," and nodes $\mathbf{111}_{5-N}$ may be referred to as "remote data nodes."

In one embodiment, each data node 115 may include a data index 130, data repository 135, data node directory 110, and data locator 120. Further, each data node 115 may include one or more data requesters 105 configured to submit requests for records related to a given individual. For example, FIG. 1 illustrates multi-node record request 125 being submitted to data locator 120.

In one embodiment, the records available from data node 115 are stored in data repository 135. Additionally, the data index 130 may provide a directory of individuals with records in data repository 135. For example, the data index 130 may include a list of demographic information related to each individual with a record in the repository 135, along with an identifier for each individual assigned by node 115. When the data requester 105 requests the records related to the given individual, the data locator 120 may be configured to determine the identifier for the individual using index 130, and to locate the individual's records in data repository 135.

Further, data requestor 105 may submit a multi-node request 125. A multi-node request 125 indicates that the data requestor 105 desires all records related to a given individual, regardless of the data node 115 in which the records are located. To optimize processing such a request, the data index $\mathbf{130}_1$ may include "remote data existence links" (or just remote data links for short). In one embodiment, the remote data links may indicate which remote data nodes $\mathbf{115}_{2-N}$ are known to have, or to not have, records related to the given individual.

To process multi-node request 125, the data locator 120 may be configured to determine whether records are available in remote data-nodes $\mathbf{115}_{2-N}$. In one embodiment, the data locator 120 makes this determination by submitting a poll request to remote data nodes $\mathbf{111}_{5-N}$. The data node directory 110 may provide a directory of all remote data nodes $\mathbf{111}_{5-N}$ that may be polled by data locator 120. Thus, the data locator 120 may obtain a list of nodes to poll from data node directory 110.

In an alternative embodiment, the multi-node request 125 may specify which remote nodes $\mathbf{115}_{2-N}$ to poll, or may specify that nodes satisfying certain criteria are polled (e.g., nodes located in particular geographic location). The data node directory 110 may include information about remote data nodes $\mathbf{115}_{2-N}$ to select a set of nodes that satisfy any criteria included in multi-node request 125. Once the set of nodes to poll is determined, data locator 120 may submit a poll to each remote data node $\mathbf{115}_{2-N}$ included in the set. Each remote node $\mathbf{115}_{2-N}$ receiving a poll request may respond with an indication of whether the remote node $\mathbf{115}_{2-N}$ has any records related to the given individual.

Additionally, in response to a poll request, a remote node $\mathbf{115}_{2-N}$ may provide a set of one or more remote data links regarding other nodes $\mathbf{115}_{2-N}$ known to have, or to not have, information related to a given individual. For example, as shown in FIG. 1, the data index $\mathbf{130}_2$ of node $\mathbf{115}_2$ includes remote data links indicating whether nodes $\mathbf{115}_3$ and $\mathbf{115}_4$ have any records regarding the given individual. When the data locator 120 of data node $\mathbf{115}_1$ submits a poll request to data node $\mathbf{115}_2$, it may respond not only with an indication of whether the polled remote node $\mathbf{115}_2$ has any relevant records, but may also provide remote data links regarding records stored by nodes $\mathbf{115}_3$ and node $\mathbf{115}_4$. In this manner, node $\mathbf{115}_1$ may determine from a response to the poll submitted to remote node $\mathbf{115}_2$ whether records regarding the individual are located in remote nodes $\mathbf{115}_3$ and $\mathbf{115}_4$, without having to poll these nodes.

In one embodiment, local node $\mathbf{115}_1$ may also provide remote data links as part of a poll request submitted to a remote data node $\mathbf{111}_{5-N}$. For example, after local node $\mathbf{115}_1$ has polled remote node $\mathbf{115}_2$, it has determined whether nodes $\mathbf{115}_3$ and $\mathbf{115}_4$ have any records regarding the given individual. When local node $\mathbf{115}_1$ subsequently polls remote node $\mathbf{115}_N$, it may provide remote data links specifying whether nodes $\mathbf{115}_{1-4}$ have any records regarding the individual.

The existence of data records in a remote node $\mathbf{115}_{2-N}$ may change over time. Accordingly, the data locator 120 may be configured to determine when a remote node $\mathbf{115}_{2-N}$ was last polled for records regarding the individual. This allows remote record links to expire after a given period of time. Alternatively, a remote node $\mathbf{115}_{2-N}$ may be configured to update a poll response, should the status of records in remote RHIO $\mathbf{115}_{2-N}$ change. For example, if remote node $\mathbf{115}_2$ had at one point provided a poll response indicating that remote node $\mathbf{115}_2$ did not have any records related to the given individual, and if such records are subsequently became available, then remote node $\mathbf{115}_2$ may be configured to provide an updated poll response to node $\mathbf{115}_1$.

One particular embodiment of the invention includes a data network 100 storing electronic health records, where each node 115 may comprise a RHIO storing (or identifying) a collection of shared electronic medical records for a plurality of RHIO participants. Each participant is a care-providing entity (e.g., a hospital, a clinic, etc) that has selected to participate in the RHIO. Detailed examples of an embodiment directed to electronic health records are described below. However, the environment 100 illustrated in FIG. 1 may be applied to many distributed domains that must be able to locate all information on a given subject across a plurality of distributed nodes (e.g. electronic databases storing criminal or arrest records maintained by different law enforcement agencies, driver's license records maintained by different states, or educational records maintained by different educational institutions, among many others examples).

Further, reference made to "patients" is understood to mean any individual for whom data is being managed in an RHIO. The individual may or may not be currently undergoing treatment or testing for medical purposes. Further, the data corresponding to the individual may or may not have been derived from medical testing or treatment (e.g., the data may have been derived from a clinical trial in which the individual voluntarily participated). Consequently, reference to "medical records" or "electronic records" includes data related to doctor visits, lab tests, hospital stays, clinical trials, diagnoses (including self-diagnoses), prognoses, records related to the purchase of healthcare related goods and services such as nutritional supplements, weight-loss programs, or records of alternative treatments such as chiropractic treatments or acupuncture treatments, etc.

Figure 2:
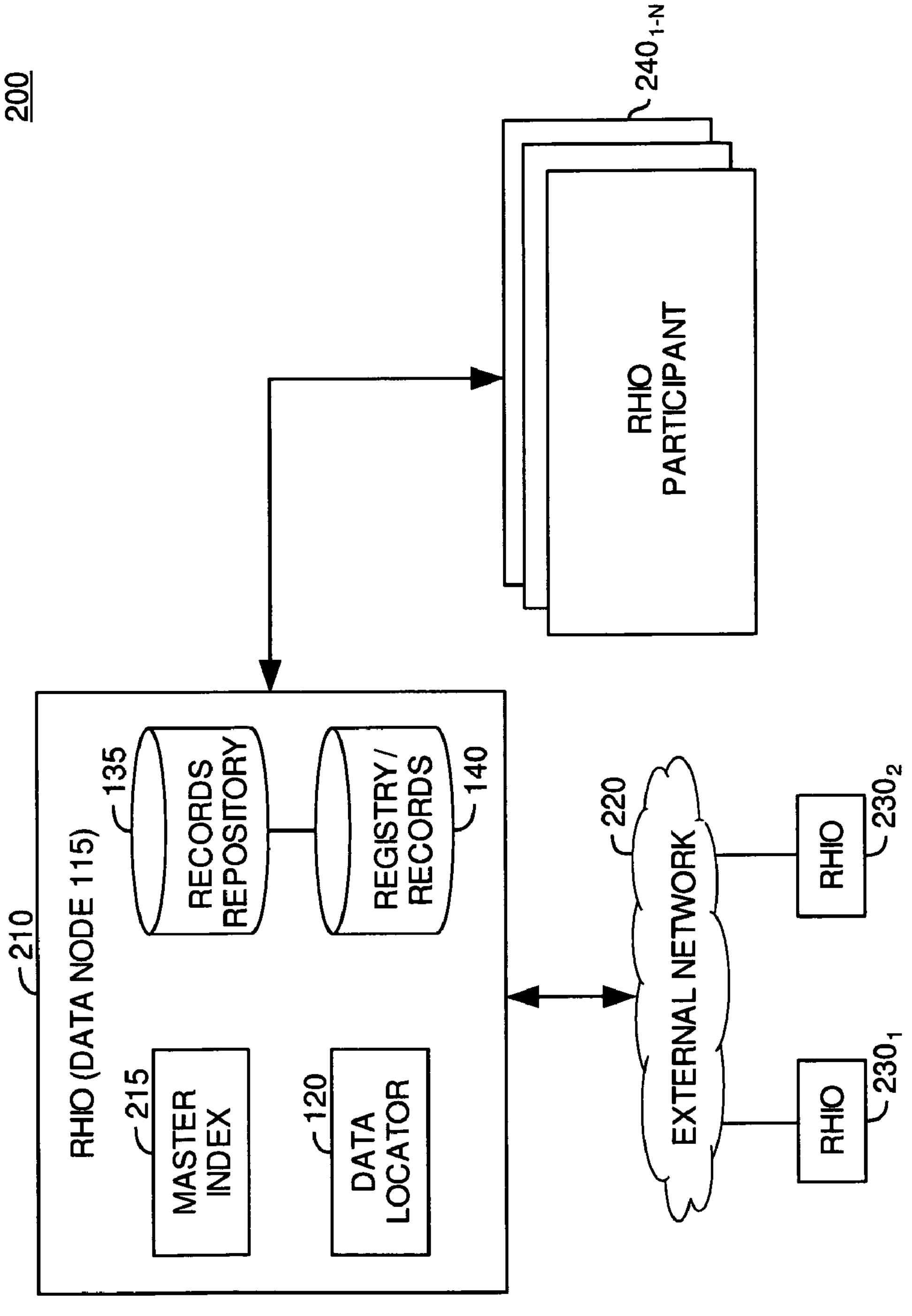
FIG. 2 illustrates an exemplary network topology for a RHIO, according to one embodiment of the invention.
Figure 3:
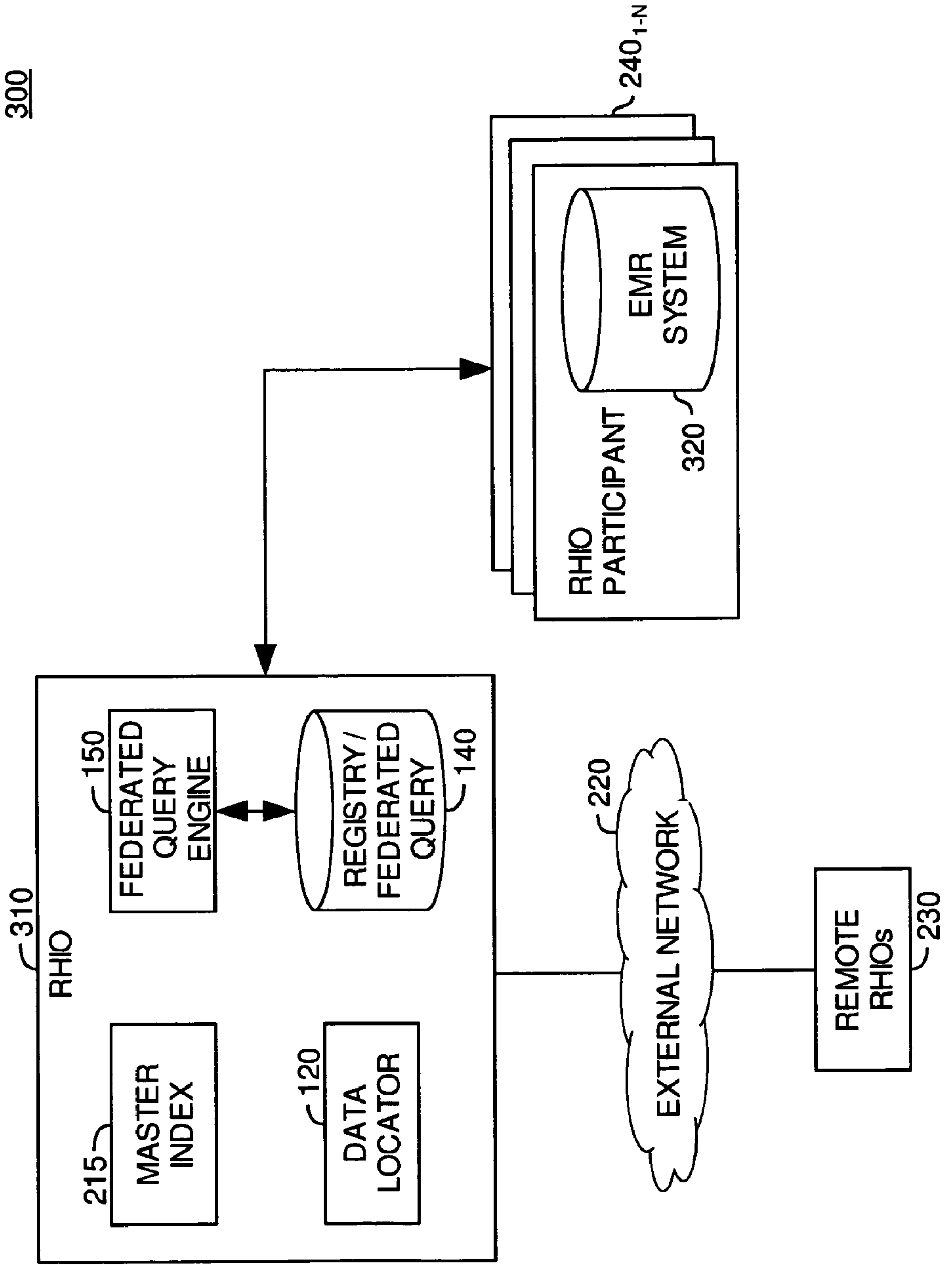
FIG. 3 illustrates an exemplary network topology for a RHIO, according to one embodiment of the invention.

In the following discussion, FIGS. 2 and 3 are used to provide an illustration of two exemplary embodiments of a regional health information organization. Each RHIO may include records related to a number of individuals receiving medical care from a participant of a given RHIO. Thereafter embodiments of the invention allowing one RHIO to locate records related to an individual that may be stored one or more remote RHIOs are described.

Additionally, as used herein, a "polling RHIO" refers to one RHIO submitting a poll request to another RHIO, and a "polled RHIO" refers to the RHIO receiving the poll request. Similarly, a "local RHIO" refers to one given RHIO, relative to others referred to as "remote RHIOs." However, these labels are used to facilitate the description of embodiments of the invention regarding poll messages exchanged between a set of RHIOs, and not to imply distinct or different types of RHIOs generally. Also, as used herein, a poll request may comprise a message transmitted from a polling RHIO to a polled RHIO. The poll request asks the polled RHIO to respond within an indication of whether the polled RHIO has or does not have electronic records regarding an individual identified in the poll request.

FIG. 2 illustrates an exemplary network topology 200 for a regional health information organization (RHIO) 210, according to one embodiment of the invention. The RHIO 210 allows a plurality of participants 240$_{1-N}$ (e.g., a hospital, clinic, pharmacy, emergency room, treatment center, claims processor, etc.) to share and exchange electronic healthcare records with one another. More generally, each participant 240 may be any organization that elects to participate in electronic record sharing as part of a given RHIO 210.

Figure 4:
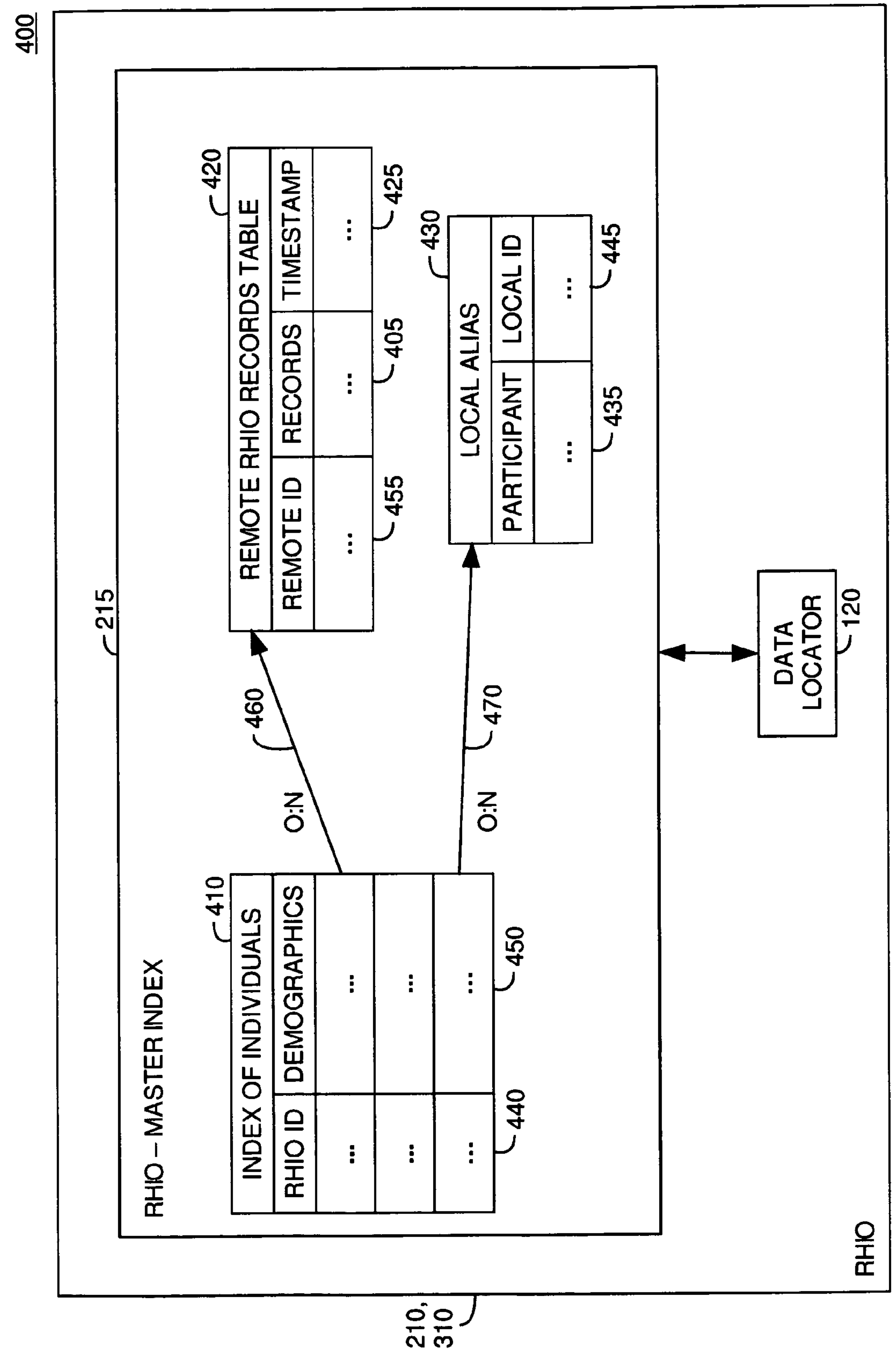
FIG. 4 illustrates a master index for a RHIO, according to one embodiment of the invention.

As shown in FIG. 2, the RHIO 210 may include a master index 215, registry 140, data locator 120, and a records repository 135. In one embodiment, the master index 215 may identify which individuals have electronic records stored in the RHIO 210. That is, the master index 215 provides a list of individuals with electronic records available within RHIO 210. In one embodiment, each individual with records available from the RHIO may be assigned a RHIO ID. The master index 215 may provide a directory of the RHIO IDs along with demographic information regarding each individual. Additionally, the master index 215 may include remote data links specifying remote RHIOs 230 known to have, or to not have records related to a given individual. One embodiment of the master index 215 is illustrated in FIG. 4, below.

In one embodiment, the registry 140 may provide an index of electronic records available in RHIO 210. The registry 140 may index the available records using the IDs assigned by the RHIO 210. The data locator 120 may be configured to locate records related to a given individual using index 140. For example, the data locator 120 may receive a request from a participant 240 to locate electronic records regarding a given individual. If the request is limited to the local RHIO 210 (i.e., the request does not indicate that records in remote RHIOs 230 should be located), then the data locator 120 consults the master index 215 to determine whether the individual identified in the request has a RHIO ID in master index 215. If so, the registry 140 may be used to determine what records are available in the data repository 135.

Additionally, the data locator 120 may be configured determine which remote RHIOs 230 have available records regarding the individual. In one embodiment, the data locator 120 transmits poll requests to a set of polled RHIOs 230 in order to determine which RHIOs 230 have electronic records regarding the individual. After receiving poll responses from the polled RHIOs 230, the polling RHIO 210 may create remote records links in the master index 215 indicating which RHIOs 230 have, or do not have, records regarding the individual. Thus, subsequent requests to locate records for this individual may be highly optimized as the master index 215 of the polling RHIO will be able to identify a complete collection of RHIOs 230 that have electronic records regarding the individual without having to transmit any additional poll requests. Further, in one embodiment, remote record data links may be included with poll requests and poll responses. Thus, the knowledge of which RHIOs have electronic records regarding a given individual may be shared during the polling process.

Illustratively, RHIO 210 centralizes the electronic records for the RHIO 210 in repository 135. This may allow the RHIO 210 to address issues such as data security, privacy, and authentication for each participant 240 participating in electronic record sharing using RHIO 210. Each participant 240 may submit electronic records to and receive records from, the RHIO 210 that are stored in repository 135. The electronic records may be stored in a common formats (e.g., XML document or .PDF) or structured (and/or ICD-9 coded) format. However, the electronic records may include any patient-related data represented in a digital form. Accordingly, text documents, images (e.g., x-rays or other imaging data) lab-test results, doctor's notes, insurance information, patient observations, and the like, may all be electronic records stored in repository 135. Thus, any record submitted by a participant 240 to the RHIO 210 may be stored in repository 135, and associated with the individual to whom the record pertains using a RHIO ID.

FIG. 3 illustrates a second exemplary network topology 300 for a RHIO 310. RHIO 310 also includes a master index 215, registry 140, and data locator 120. These components may operate in the manner described above regarding RHIO 210 in FIG. 2. Rather than store records using repository 135, however, RHIO 310 stores records using a decentralized or federated approach. The registry 140 may be used to identify which participants 240 have records regarding a particular individual. Doing so allows a given participant 240 to each store data in a data repository 320 located at the participant 240. Federated query engine 150 may be configured to retrieve records from participants 240. Additionally, like the RHIO 210 described in reference to FIG. 2, data locator 120 may be used to poll other RHIOs 230 over external network 220 to determine whether records are available regarding a given individual in remote a remote RHIO 230.

In another embodiment, a RHIO may adopt a hybrid approach to the storage of electronic records for the RHIO. In such a case, a storage repository 135 may be used to store some data records, while other records may be stored by some of the participants 240 in the repository 320 using a decentralized approach. For example, a first participant 240 may comprise a large hospital or research institution that maintains an extensive IT infrastructure. Such a first participant 240 may chose join a RHIO, and allow other participants 240 to access data records from records repository 320. At the same time, a second participant 240 (e.g., a small clinic), may wish have electronic records in a repository 135 maintained by the RHIO.

As stated above, the master index 215 may identify which individuals have electronic records stored in a RHIO (e.g., RHIOs 210 and 310). The master index 215 associated with a given RHIO may include remote record data links identifying remote RHIOs 230 known to have, or to not have records related to a given individual. In one embodiment, remote data links regarding the existence of records for a given individual may be exchanged when the data locator 120 of a polling RHIO transmits a poll request to a set of polled RHIOs to locate electronic records. FIGS. 4-7 illustrate embodiments of the invention that allow a local RHIO (e.g., RHIOs 210 and 310) to determine which remote RHIOs 230 have records related to a given individual.

First, FIG. 4 illustrates an embodiment of the master index 215. As shown, the master index 215 includes table 410 that provides an index of individuals with records stored by a given RHIO. Each individual in table 410 may be identified within the RHIO by an assigned RHIO ID 440. The demographic information 450 may be used to determine the RHIO ID for a given individual. For example, the RHIO ID 440 assigned to a given individual may be determined by cross referencing a name, age, social security number, or other demographic information 450 stored in table 410 with a RHIO ID 440. The demographic information 450 may be provided to a polled RHIO as part of a poll request. In response, the polled RHIO may use the demographic information 450 to determine whether the master index 215 of the polled RHIO includes an entry for the individual identified in the poll request.

Additionally, the information in table 410 may be cross referenced with local alias table 430. Local alias table 430 may cross reference a list of local IDs used by RHIO participants 240 with the RHIO ID 440. Local alias table 430 allows a participant 240 to maintain a preexisting local ID for a given individual. For example, a hospital may reference each individual using a unique patient number. The patient number may be stored as an entry in local alias table 430, cross referenced to the RHIO ID 440 assigned to the individual. As shown, each individual (as identified by a RHIO ID 440) may include zero or more reference links 470 in local alias table 430. Each row of table 430 identifies a participant 435 and a local ID 445 used by the participant 240 to identify the individual.

Thus, when a participant 240 submits a request to locate electronic records, the request may identify the individual that is the subject of the request using a local ID (e.g., a patient number). In one embodiment, a given participant 240 may not have, or may not be permitted to access, demographic information 450 regarding a given individual. For example, a technician submitting a request to locate electronic records may not have access to an individual's social security number. However, by including a local ID 445 with a request, the data locator 120 may be able to determine a RHIO ID 440 for the individual using alias table 410. Using this RHIO ID 440, the data locator 120 may retrieve demographic information 450 for the individual from the master index 215. The polling data locator 120 may then provide this demographic information 450 as part of a poll request transmitted to a polled RHIO. In turn, the polled RHIO may determine a RHIO ID 440 used by the polled RHIO to identify the individual. This identification process may be repeated by each polled RHIO. In another embodiment, if no local ID is provided with a request, then a participant 240 may provide any available demographic information 450 that the data locator 120 may use to determine a RHIO ID 440 associated with the individual that is the subject of a request.

In one embodiment, master index 215 may include remote RHIO records table 420. The records table 420 may identify remote RHIOs 230 known to have, or to not have records regarding an individual identified in table 410. Illustratively, each row of remote RHIO records table 420 includes the identity 455 of a particular remote RHIO 230, an indication 465 of whether the particular remote RHIO 230 stores any records related to a given individual, and an indication 425 of when a remote RHIO 230 was last polled. Collectively, each row of table 420 is referred to as a remote records data link 460. As shown, each entry identifying a particular individual in table 410 may be cross referenced with zero or more remote data links 460 in remote records table 420.

When a polled RHIO receives a poll request to determine whether records related to a given individual exist in the polled RHIO, the polled RHIO may be configured to provide an indication of whether it has any electronic records available as part of a poll response. In addition, the polled RHIO may also provide any remote record data links 460 as part of a poll response. This allows the polling RHIO to learn whether a RHIO identified in a remote records data link 460 has any electronic records available, without having to submit a poll request to the RHIO identified in a remote records links 460

In one embodiment, the participant 240 may submit a request to locate a comprehensive collection of medical records related to a particular individual. In response, the data locator 120 may be configured to determine which remote RHIOs 230 have such records. First, the data locator 120 may be configured to identify the subject of a request, for example, by cross referencing a participant's local ID 445 with a RHIO ID 440 for a given individual. Once a RHIO ID 440 is determined, the demographic information 450 associated with RHIO ID 440 may be transmitted to remote RHIOs 230 as part of a polling message. The poll asks the remote RHIOs to determine whether any records are available regarding the individual identified in the poll. After determining a set of RHIOs known to have records related to the individual is determined, any relevant electronic records may be assembled by retrieving the records from RHIOs identified to have records regarding the individual.

Figure 5:
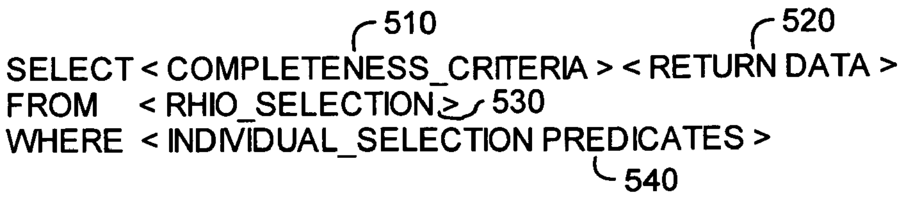
FIG. 5 illustrates a multi-node query using an SQL-like grammar, according to one embodiment of the invention.

In one embodiment, the request submitted by a participant 240 may specify a particular set of RHIOs to poll, and optionally, criteria identifying how comprehensive of a search to perform. FIG. 5 illustrates components of a record request supplied as part of a multi-node request 125 using an SQL-like grammar. The request grammar illustrated in FIG. 5 is provided solely for illustrative purposes, and other request grammars may be used. As illustrated in FIG. 5, the multi-node request 125 includes four components: <completeness_criteria> 510, <return_data> 520, <RHIO_selection> 530 and, <individual_selection_predicates> 540. Different embodiments may provide some, or all of the illustrated components, or may provide different components to allow a participant 240 to submit a request to locate records regarding a given individual.

The <completeness_criteria> 510 indicates whether the participant 240 is requesting all electronic records associated with a given individual, or a subset thereof. For example, allowed values for this query component may include "ALL"

(retrieve all records across RHIOs specified in RHIO selection component 530), or a request may be limited to a specific number of records to retrieve before halting the search. The <return_data> component 520 specifies which electronic records should be returned in response to the query.

The <RHIO_selection> component 530 may be used to indicate the set of RHIOs to include when searching for records regarding the individual. In one embodiment, the data locator 120 may default to locating only records from the RHIO that includes the participant 240 submitting the request 125. The <RHIO_selection> component 530 may specify that records from remote RHIOS should also be located in response to the request 125. For example, a <RHIO_selection> component 530 included in the multi-node record request 125, may use a "wildcard" value such as the "*" character to indicate that all records from any known RHIO should be located. Alternatively, a particular set of remote RHIOs 230 may be specified. As another alternative, <RHIO_selection> component 530 may provide selection criteria (e.g. find records for Individual X from RHIOs located in Minnesota). As described above regarding FIG. 1, a data node directory 110 may provide a directory of remote RHIOs that may be polled. In one embodiment, the data locator 120 may use information from the data node directory 110 to determine a set of RHIOs to poll in order to locate records regarding an individual identified in request 125.

The <individual_selection_predicates> 540 may be used to specify the individual that is the subject of the request. That is, it identifies whose electronic records the participant 240 is requesting the data locator 120 to locate. Accordingly, in one embodiment, <individual_selection_predicates> 540 may include a local ID 445, used by participant 240 to identify the individual and available demographic attributes 450. The data locator 120 may use this information to cross reference the local ID 445, with the RHIO ID 440. In one embodiment, the request 125 may include additional conditions, such as what type of record the participant 240 is requesting. For example, a request 125 may specify that data locater 120 should locate a comprehensive collection X-rays for the individual.

Figure 6:
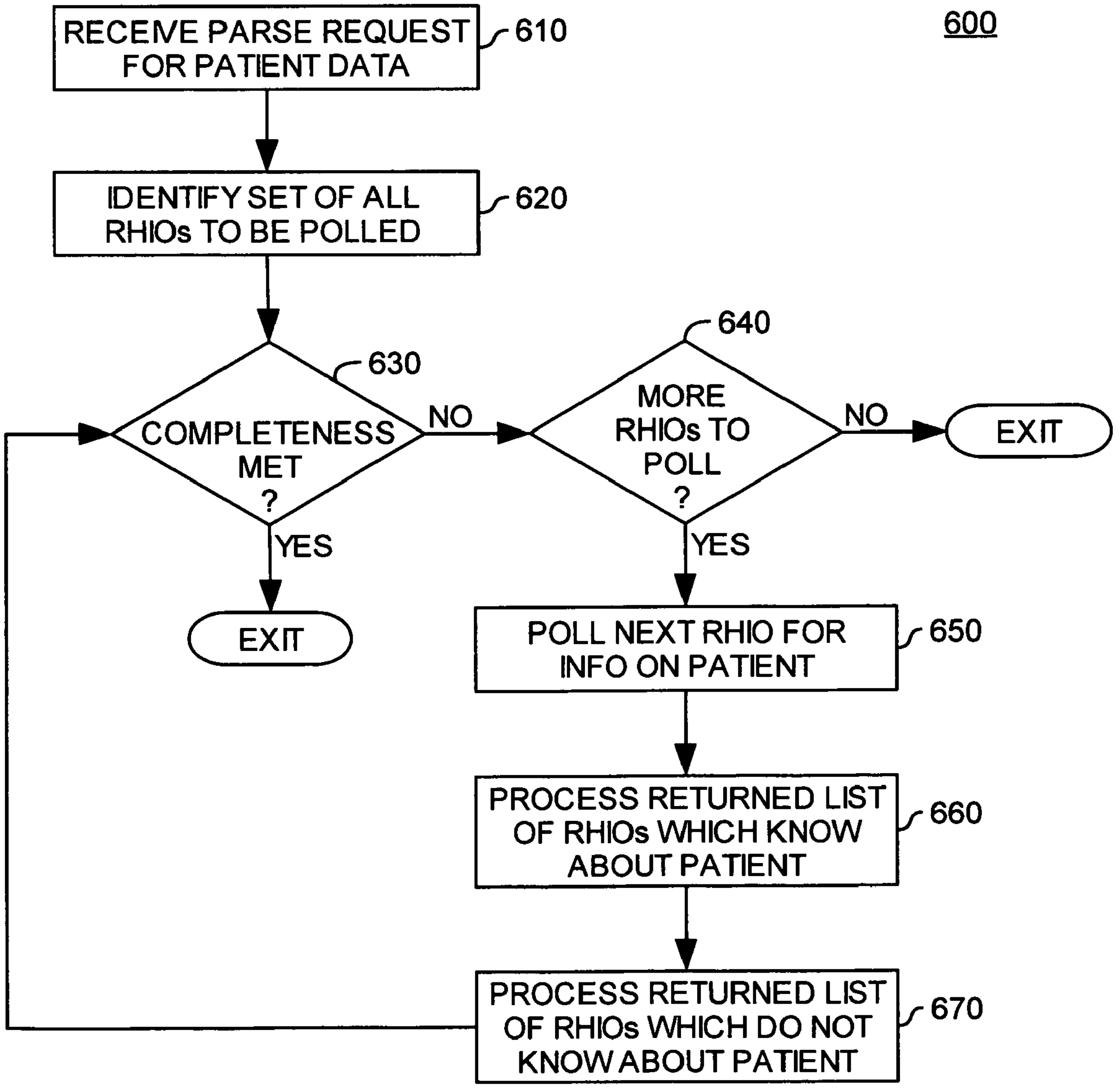
FIG. 6 illustrates a method for processing a request to locate electronic records, according to one embodiment of the invention.

FIG. 6 illustrates a method 600 for a polling RHIO to determine a set of RHIOs that have electronic records regarding a given individual, according to one embodiment of the invention. At step 610, the data locator 120 receives a request to locate records for the given individual. If the data locator 120 determines the request does not specify records from remote RHIOs should be located, then the request may be processed without regard to remote RHIOs 230. In such a case, the RHIO ID 440 for the individual specified in the request is identified, and registry 140 may be used to locate records in repository 135 that are available from the RHIO.

Alternatively, if the request specifies that records from remote RHIOs 230 should be located, then data locator 120 may be configured to poll a set of remote RHIOs to determine which ones store records related to the individual. At step 620, the <RHIO_selection> component 530 is used to determine a set of remote RHIOs 230 to be polled. For example, the data locator 120 may determine a set of remote RHIOs 230 listed in directory 110 that satisfy any <RHIO_selection> criteria. Alternatively, all RHIOs listed in directory 110 may be polled. Before transmitting poll requests to the set of remote RHIOs 230, however, the data locator 120 may retrieve data links 460 from records table 420. In one embodiment, the data locator 120 may be configured to skip submitting a poll request to any RHIOs identified in a remote records data link 460. Also, the data links 460 may be included in subsequent poll messages transmitted to additional polled RHIOs 230. Thus, a poll request may not only request information from a polled RHIO 230, but may also inform the polled RHIO 230 regarding RHIOs known to have, or to not have electronic records regarding the individual that is the subject of the poll request.

At step 630, the data locator 120 determines whether any completeness criteria specified in the request is satisfied. For example, if the remote record table 420 identifies an adequate number of remote RHIOs 230 known to have electronic records related to the patient, or if a sufficient number of RHIOs have been polled, the method proceeds to step 670 and terminates. Otherwise, the data locator 120 polls a remote RHIO to learn whether the remote RHIO has any records regarding the individual. At step 640, a loop begins that includes step 650, 660, 670, and 630. During each iteration of the loop, a poll request is sent to a remote RHIO 230. In one embodiment, the remote RHIO 230 provides a poll response indicating whether the remote RHIO 230 has any records related to the individual. Furthermore, the poll response may also include remote record links 460 indicating other remote RHIOs 230 known to have (or to not have) records regarding the individual.

The loop begins at step 650 where a RHIO from the set selected at step 620 is polled to determine whether it includes electronic records related to the individual. In one embodiment, the data locator 120 of a given RHIO (210, 310) sends the RHIO ID 440 and the demographic attributes 450 for the individual to a remote RHIO 230 being polled. The remote RHIO 230 receiving the poll request uses this information to first determine whether an entry in the master index 125 of the remote RHIO exists for the individual. If so, then records are available for this individual from the remote RHIO 230, and the poll is answered affirmatively.

In addition, a polled RHIO 230 may have remote records data links 460 indicating other RHIOs known to have, or to not have, records related to the individual identified in the poll request. If so, the polled RHIO 230 may include the data links 460 in a poll response transmitted to a polling RHIO. Similarly, the polling RHIO may include remote records data links 460 regarding other RHIOs known to have, or to not have electronic records related to the individual. This information may be recorded by the polled RHIO 230 in its master index 215. Thereafter, if one of the polled RHIOs receives a request to locate records regarding the given individual, then the polled RHIO may avoid polling some or all of the potential RHIOs.

In one embodiment, the polling RHIO performs steps 660 and 670 to process a response to a poll request. First, the polling RHIO may create a remote data link 460 indicating whether the polled RHIO has any records regarding the individual identified in the poll request. In addition, a polled RHIO may include a list of remote record data links 460 as part of a poll response. Using this list, the data locator 120 of the polling RHIO may be configured to update its master index 215 to record any links 460 included in the poll response in remote record table 420. Additionally, if the poll response includes a link 460 corresponding to a remote RHIO 230 that is also in the set of RHIOs to be polled, such a RHIO may be removed from the set.

After processing a poll response, the method 600 returns to step 630 and determines whether a sufficient number of RHIOs have been polled, according to <completeness_criteria> 510. If not, the polling RHIO begins another iteration of steps 650 through 670.

Although the method 600 illustrates a serial polling process, other embodiments of the invention may perform a parallel or partially parallel polling process. In such embodiments, a polling RHIO may transmit a poll request to multiple polled RHIOs simultaneously. After the polling RHIO receives responses from the polled RHIOs, the polling RHIO may update its master index 215 with the set of poll responses and any remote record data links 460 transmitted with the responses. Additionally, the polling RHIO may be configured to resolve any conflicts in poll responses. For example, where a first response indicates that a given RHIO has electronic records regarding the individual, and a second response indicates that the same particular RHIO does not have any such records, the polling RHIO may be configured to disregard any remote record data links 460. In such a case, the polling RHIO may transmit a poll request to clarify the status of the particular RHIO.

Furthermore, once each of the polled RHIOs has provided a poll response, the polling RHIO may broadcast a follow-up message to the set of polled RHIOs. In the follow-up message, the polling RHIO may provide the polled RHIOs with a set of remote data links 460. This allows the polling RHIO to share a comprehensive set of data links 460 for a given individual 460 with the each of the polled RHIOs. Thereafter, if the polling RHIO, or one of the polled RHIOs, receives a request to locate electronic records regarding the given individual, then a comprehensive set of RHIOs that have electronic records regarding the individual may be determined without any poll requests being transmitted at all. In other words, once the first round of poll requests and responses are exchanged, each RHIO may have an up-to-date set of data links regarding the existence of electronic records in the set of polled RHIOs.

Additionally, as a RHIO processes poll responses, the date/time at which a particular RHIO was polled may be recorded (e.g., in timestamp column 470 of remote record table 420). Because the state of a given RHIO may change over time, a RHIO known to not have records relating to a given individual, may subsequently obtain such records. Accordingly, embodiments of the invention may be configured to determine whether electronic existence data may have become inaccurate or obsolete.

For example, in one embodiment, remote record data links 460 provided by with a poll response from a remote RHIO may be associated with an expiration date. If so, a data locator 120 may be configured to ignore (or delete) a particular data link 460 once it is a certain age (e.g., one day, one week, one year, etc). If remote record data links 460 from a remote RHIO 230 has expired, the remote RHIO 230 may be polled to discover the current status of records within the remote RHIO 230.

In an alternative embodiment, a polled RHIO may periodically review past poll requests responded to, and selectively notify the respective polling RHIOs of a change in the status of the polled RHIO (such as when new records have become available within the polled RHIO since responding to a given poll request). In one embodiment, the notification may include only an indication of the status change without specifying the particular information that has changed. In response, the RHIO receiving an update modifies its master index 125 to indicate the change of status regarding the existence of electronic records for the given individual. In another embodiment, the notification may specify the particular data that has changed, allowing the polling RHIO being notified to update its data records. If the RHIO had also shared the (now inaccurate) electronic records existence data with other remote RHIOs, then the change in status (or the changed information itself) may be propagated to these other RHIOs as well.

Figure 7:
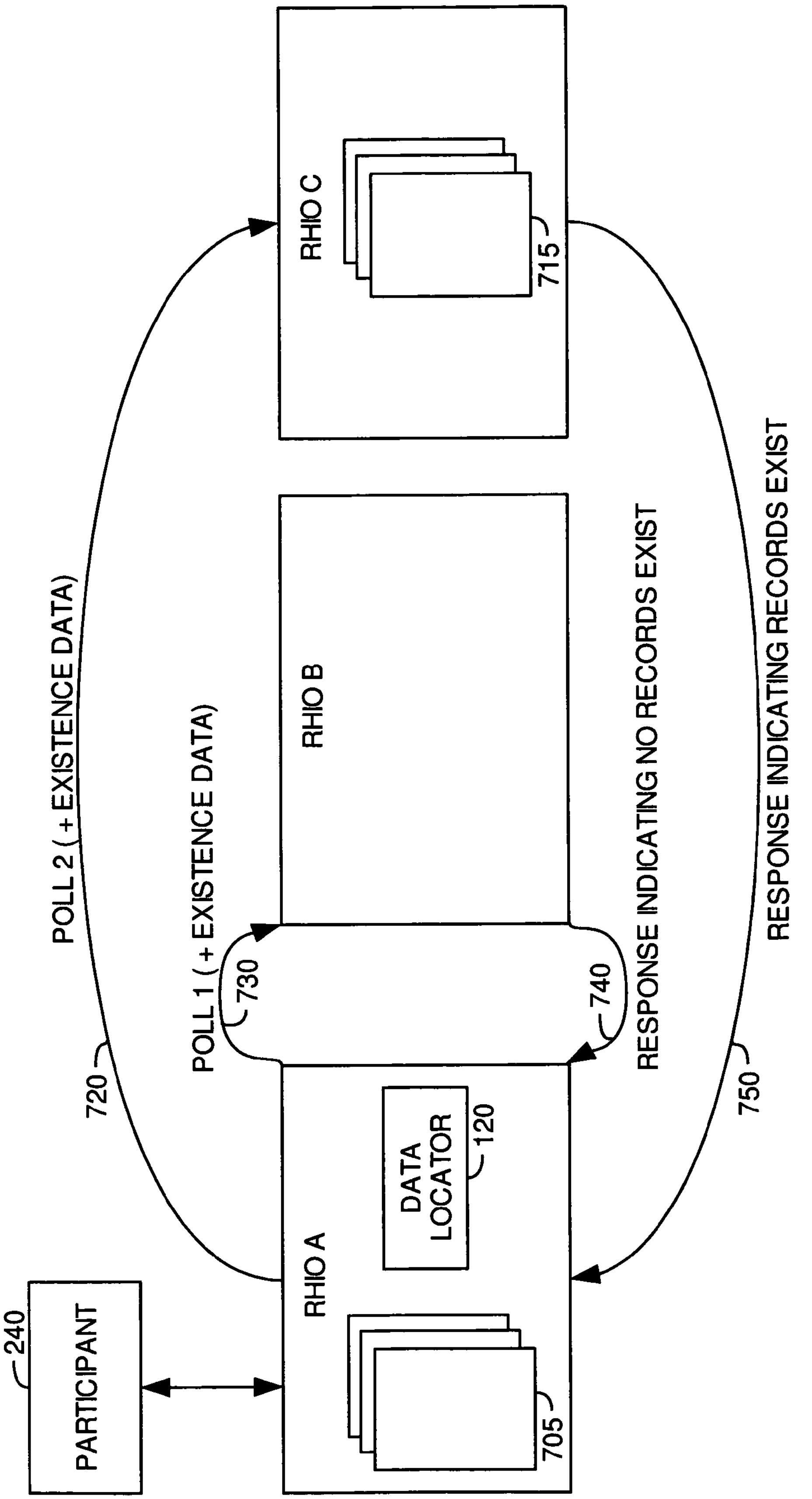
FIG. 7 illustrates a plurality of message exchanged between three distributed data nodes to share electronic records existence data, according to one embodiment of the invention.

FIG. 7 illustrates an example of three RHIOs (RHIO A, RHIO B, and RHIO C) sending and responding to poll messages, according to one embodiment of the invention In this example, RHIO A and RHIO C include data records 705 and 715 related to a particular individual. When a participant 240 of RHIO A submits a request to locate records related to this individual, the data locator 120 polls RHIO B and RHIO C, as represented by poll 1 arrow 720 and poll 2 arrow 730. First, RHIO A transmits a poll request to RHIO B. Along with the poll request, RHIO A transmits a remote record data link 460 indicating that RHIO A is known to have records related to the individual (i.e., records 705).

In processing the poll request, RHIO B determines that it does not have any records related to the individual. This information is transmitted to RHIO A in a poll response message, as indicated by poll 1 response arrow 730. RHIO B also updates its master index 215 to indicate that RHIO A has records related to the individual.

RHIO A then transmits a poll request to RHIO C. The poll request transmitted to RHIO C includes remote record data links 460 indicating that RHIO A has records regarding the individual. Further, because RHIO A has received a poll response from RHIO B, the poll transmitted to RHIO C includes a remote record data links 460 regarding RHIO B, as well. In processing the poll request, RHIO C determines that it does have records related to the individual (i.e., records 715). This information is transmitted to RHIO A, as indicated by poll 2 response arrow 730. Also, RHIO C updates its master index 215 to indicate (1) that RHIO A does have records related to the individual, and (2) that RHIO B does not. From this exchange, RHIOs B and C have learned that RHIO A has records regarding the individual, without having to poll RHIO A. Similarly, RHIO C has learned that RHIO B does not have information related to the patient, without ever querying RHIO B. Subsequently, when a participant 240 in RHIO A requests records related to the individual, it can be determined that only RHIO C needs to be contacted to retrieve records.

Thus, the status of each of the three RHIOS is updated and more knowledgeable about which records are in others. By sharing remote record data links as part of the poll requests and poll responses, each RHIO becomes more knowledgeable about which RHIOs have records regarding particular individuals. Doing so decreases network traffic, and leads to more efficient data retrieval. Those skilled in the art will recognize that this method of implementing cross RHIO queries has a number of distinct advantages over other approaches. For example, embodiments of the invention do not require a nation-wide, master patient index to identify all RHIOs that have electronic health records regarding a given individual. This avoids the technical complexity and privacy issues that would have to be resolved to create a massive central index. In many cases, embodiments of the invention will identify a complete set of all RHIOs containing data for a given individual, without the need to poll each RHIO for this information. If there have been any previous polls for the records related to a given individual, embodiments of the invention require less polling than a brute-force approach.

Furthermore, subsequent requests for information for the same patient will be greatly optimized since the master index 215 of the requesting RHIO has complete information regarding which remote RHIOs 230 contain data for the patient. Because requests for electronic records related to a given individual may be infrequent and bursty, once the set of RHIOs that have electronic records related to a given individual, a number of subsequent requests may be processed in a highly efficient manner. For example, consider again the unconscious patient in an emergency room. An initial request for record access may determine the set of RHIOs that contain data for the individual. Thereafter, as the individual receives care, a number of follow up queries may be directed to the RHIOs known to have information related to the individual, without the need for polling at all. Once the patient is discharged, the patient may go some time without receiving any further medical care. In such a case, the remote data links shared among a plurality of RHIOs may expire. Thus, for the period when requests are most likely to occur, each RHIO may be aware of what RHIOs to contact for information regarding the individual. Furthermore, rather than maintain a massive nationwide index at each RHIO, remote records data may be shared among RHIOs for individuals with records commonly accessed from multiple RHIOs, without also maintaining records existence data for individuals whose records are not the subject of requests for records from other RHIOs.

While the foregoing is directed to embodiments of the present invention, other and further embodiments of the invention may be devised without departing from the basic scope thereof, and the scope thereof is determined by the claims that follow.

What is claimed is:

1. A computer-implemented method comprising:

accessing a plurality of electronic records associated with an identified subject, wherein, the electronic records exist in a plurality of independent data nodes, the accessing comprising:

receiving, from a first data node, a response to a poll request, wherein the response includes an indication of whether records regarding the identified subject are available in the first data node; and polling at least a second data node to determine an availability of electronic records regarding the identified subject at the second data node, wherein the poll transmitted to the second data node includes the indication received from the first node, wherein the plurality of independent data nodes are geographically distributed nodes storing electronic health records.

2. The method of claim 1, wherein the indication received from the first node includes a further indication of at least one additional node, from the plurality of independent data nodes, known to have, or to not have, electronic records regarding the identified subject.

3. The method of claim 1, wherein the poll request, includes an indication of at least one additional node, from the plurality of independent data nodes, known to have, or to not have, electronic records regarding the identified subject.

4. The method of claim 1, further comprising:

prior to receiving the response to the poll request, receiving a request to locate the plurality of electronic records associated with the identified subject;

selecting at least one data node as the first data node to poll to determine the availability of records regarding the identified subject; and submitting the poll request to the first data node.

5. The method of claim 4, wherein selecting at least one data node to poll comprises, selecting a plurality of data nodes, and wherein submitting the poll request to the first data node comprises transmitting the poll request to each of the selected nodes in parallel.

6. The method of claim 4, wherein selecting at least one data node comprises, selecting a plurality of data nodes, and wherein each of the selected nodes are polled sequentially, and wherein existence data regarding the availably of electronic records regarding the known subject received from each previously polled node, of the sequence, is transmitted to each subsequently polled node of the sequence.

7. The method of claim 4, wherein the request to locate the plurality of electronic records associated with the identified subject further specifies a set of data nodes to be polled.

8. The method of claim 1, wherein the request includes a local ID used by a requesting entity to identify the identified subject, wherein a given data node identifies the identified subject using an ID assigned by the given node, and wherein the ID assigned by the given data node is cross referenced with the local ID used by the requesting entity using an entry in an alias table.

9. The method of claim 1, wherein each of the plurality of independent data nodes comprises a regional health information organization (RHIO) that includes a plurality of participants, and wherein the identified subject is an individual with electronic health records available from at least one of the RHIOs.

10. The method of claim 9, wherein each RHIO includes a master index that lists the individuals with electronic records available from a respective RHIO, and wherein the master index is configured to store information regarding the availability of electronic records in one or more of the other RHIOs.

11. The method of claim 9, wherein each of the RHIOs assigns a RHIO ID to each individual with electronic records in a given RHIO, and wherein each RHIO maintains a master index of assigned RHIO IDs that is cross referenced with at least one local ID used by an organization participating in the RHIO.

* * * * *